(12) United States Patent
Schumaier

(10) Patent No.: US 11,546,702 B1
(45) Date of Patent: Jan. 3, 2023

(54) CUSTOM ELECTRONIC SWITCHABLE HEARING PROTECTION SYSTEM

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 0 days.

(21) Appl. No.: 17/887,548

(22) Filed: Aug. 15, 2022

(51) Int. Cl.
*H04R 25/00* (2006.01)

(52) U.S. Cl.
CPC ..... *H04R 25/505* (2013.01); *H04R 2225/025* (2013.01); *H04R 2225/61* (2013.01)

(58) Field of Classification Search
None
See application file for complete search history.

(56) References Cited

U.S. PATENT DOCUMENTS

| | | | |
|---|---|---|---|
| 4,985,925 A | 1/1991 | Langberg et al. | |
| 6,661,901 B1 | 12/2003 | Svean et al. | |
| 7,024,010 B2 | 4/2006 | Saunders et al. | |
| 7,512,243 B2 | 3/2009 | Haussmann | |
| 10,045,133 B2 | 8/2018 | Bauman et al. | |
| 10,937,407 B2 | 3/2021 | Goldstein | |
| 2016/0255449 A1* | 9/2016 | Bauman | G10K 11/16 381/329 |
| 2020/0288251 A1* | 9/2020 | Kuipers | H04R 25/456 |
| 2021/0052429 A1 | 2/2021 | Dittrich et al. | |

* cited by examiner

*Primary Examiner* — Kenny H Truong
(74) *Attorney, Agent, or Firm* — Luedeka Neely Group PC

(57) ABSTRACT

An electronic hearing protection system includes an electronic hearing device having a housing that is disposed in a recessed cavity in an earplug. The housing of the electronic hearing device is configured to be rotatable between multiple positions, including a first position in which a speaker of the electronic hearing device aligns with a sound tube in the earplug to permit sound generated by the speaker to travel through the sound tube to the user's ear canal, and a second position in which the housing blocks the sound tube to at least partially prevent sound from reaching the user's ear canal.

15 Claims, 4 Drawing Sheets

CUSTOM ELECTRONIC SWITCHABLE HEARING PROTECTION SYSTEM

FIELD

This invention relates to the field of electronic hearing protection. More particularly, this invention relates to a system for electronic hearing protection that features an earplug and an electronic hearing device, where the electronic hearing device is switchable between multiple positions, including a position that permits sound to reach the user's ear and another position that at least partially prevents sound from reaching a user's ear.

BACKGROUND

Hearing aids enhance a user's hearing by transmitting sound through a speaker in the hearing aid and into the inner ear of the user. However, a problem exists if a user requires a hearing aid and also requires hearing protection, such as in military, industrial, hunting or loud musical settings. Therefore, there is a need for a device that allows users to easily switch between hearing aid functionality and hearing protection functionality.

Previous hearing protection devices, such as earplugs, adequately block out unwanted sound but provide no path for desired sound to travel. In other words, the user must take out the earplug out to hear the desired sound. Current hearing protection devices (such as described in U.S. Pat. No. 7,512,243B2 and US20210052429A1) provide hearing protection that involves manual operation of a movable structure to unblock some form of opening to allow sound through to the user's ear. These devices require manual sliding or rotation of the movable structure to alter the level of sound attenuation, but they do not provide for an electronic hearing device within the system. U.S. Ser. No. 10/045,133B2 describes a system that includes an electronic hearing device, but the electronic hearing device is external to the hearing protection system in a bulky and cumbersome orientation.

Thus, current hearing protection systems do not provide easy access to switch between quality sound filtering and adequate noise obstruction.

What is needed, therefore, is a device that allows users to easily switch between a hearing aid mode and a hearing protection mode, that provides for electronic programmability of hearing aid functions, and that fits comfortably, securely, and discreetly in the user's ear.

SUMMARY

The above and other needs are met by a custom electronic switchable hearing protection system that includes an earplug and an electronic hearing device. The earplug includes a first portion, a second portion and sound tube that extends through the first portion and the second portion. The first portion is configured to be placed in the user's outer ear and the second portion is configured to go in the user's ear canal. The first portion includes a recessed cavity having an inner profile. The sound tube includes a first opening disposed within the recessed cavity of the first portion and a second opening disposed at a distal end of the second portion.

In preferred embodiments, the electronic hearing device is received at least partially within the recessed cavity of the earplug. The electronic hearing device includes a housing that contains a speaker and other electronic components. The housing includes a front surface, a rear surface opposite the front surface, a side surface, and a speaker opening in the rear surface. The side surface, which is disposed between the front and rear surfaces, has an outer profile that corresponds to the inner profile of the recessed cavity in the earplug. The speaker opening is configured to emit sound from the speaker.

The housing is configured to be rotatable between a first position and a second position. In the first position, the speaker opening aligns with the first opening of the sound tube, thereby permitting the sound generated by the speaker to propagate through the sound tube to the second opening. In the second position, the rear surface of the housing at least partially blocks the first opening of the sound tube, thereby at least partially preventing sound from entering the sound tube.

In some embodiments, the hearing protection system includes a grip portion extending out from the front surface. The grip portion is configured to be gripped by the user for rotating the housing. In some embodiments, the grip portion comprises a rotatable circular structure with at least one tab configured to be gripped by the user.

In some embodiments, the earplug is shaped to fit the shape of the user's ear canal.

In some embodiments, the earplug is made of silicone.

In some embodiments, the housing of the electronic hearing device is made of plastic.

In some embodiments, the electronic hearing device incorporates programmable digital signal processing, allowing the device to be programmed according to the user's hearing profile.

In some embodiments, the housing is configured to rotate 180 degrees from the first position to the second position.

In some embodiments of the electronic hearing system, a protrusion extends outward from the rear surface of the housing and is spaced apart from the speaker opening. The protrusion is configured to align with and at least partially block the first opening of the sound tube when the housing is rotated to the second position.

In some embodiments of the hearing protection system, an indentation in a surface of the recessed cavity engages the rear surface of the housing. The indentation is configured to at least partially receive the protrusion when the housing is in the first position.

In some embodiments, the hearing protection includes a push button disposed on the front surface of the housing of the electronic hearing device. The push button is configured to be pressed by a user to power-on or power-off the electronic hearing device, The push button can also be used adjust the sound generated by the speaker.

In some embodiments, the inner profile of the recessed cavity is cylindrical, and the side surface of the housing is cylindrical.

In some embodiments, the electronic hearing device incorporates fast compression programming to immediately shut off sound amplification upon detection of a loud noise, and to resume amplification after the loud noise ends.

In some embodiments, an annular protrusion extends outward from the side surface of the housing of the electronic hearing device. In these embodiments, the housing is disposed within an outer ring having an outer profile configured to correspond to the inner profile of the recessed cavity. The outer ring also includes an annular channel on its inner surface configured to engage the annular protrusion on the housing, thereby securely holding the housing within the outer ring while simultaneously allowing for rotation of the housing within the outer ring.

In another aspect, embodiments of the invention are directed to a method for using a hearing protection system that includes an earplug having a recessed cavity and a sound tube, and an electronic hearing device disposed within the recessed cavity. The method includes:

inserting the earplug of the hearing protection system into a user's ear canal;

rotating the electronic hearing device within the recessed cavity to a first position in which a speaker of the electronic hearing device aligns with the sound tube in the earplug, thereby permitting sound from the speaker to propagate through the sound tube into the user's ear canal; and rotating the electronic hearing device within the recessed cavity to a second position in which a protrusion on the electronic hearing device aligns with and at least partially blocks the sound tube, thereby at least partially preventing sound from entering the sound tube and the user's ear canal.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 3 depicts a cross-sectional side view of the hearing protection system in which an electronic hearing device portion of the system is removed from an earplug portion of the system; and.

DETAILED DESCRIPTION

Figure 1:
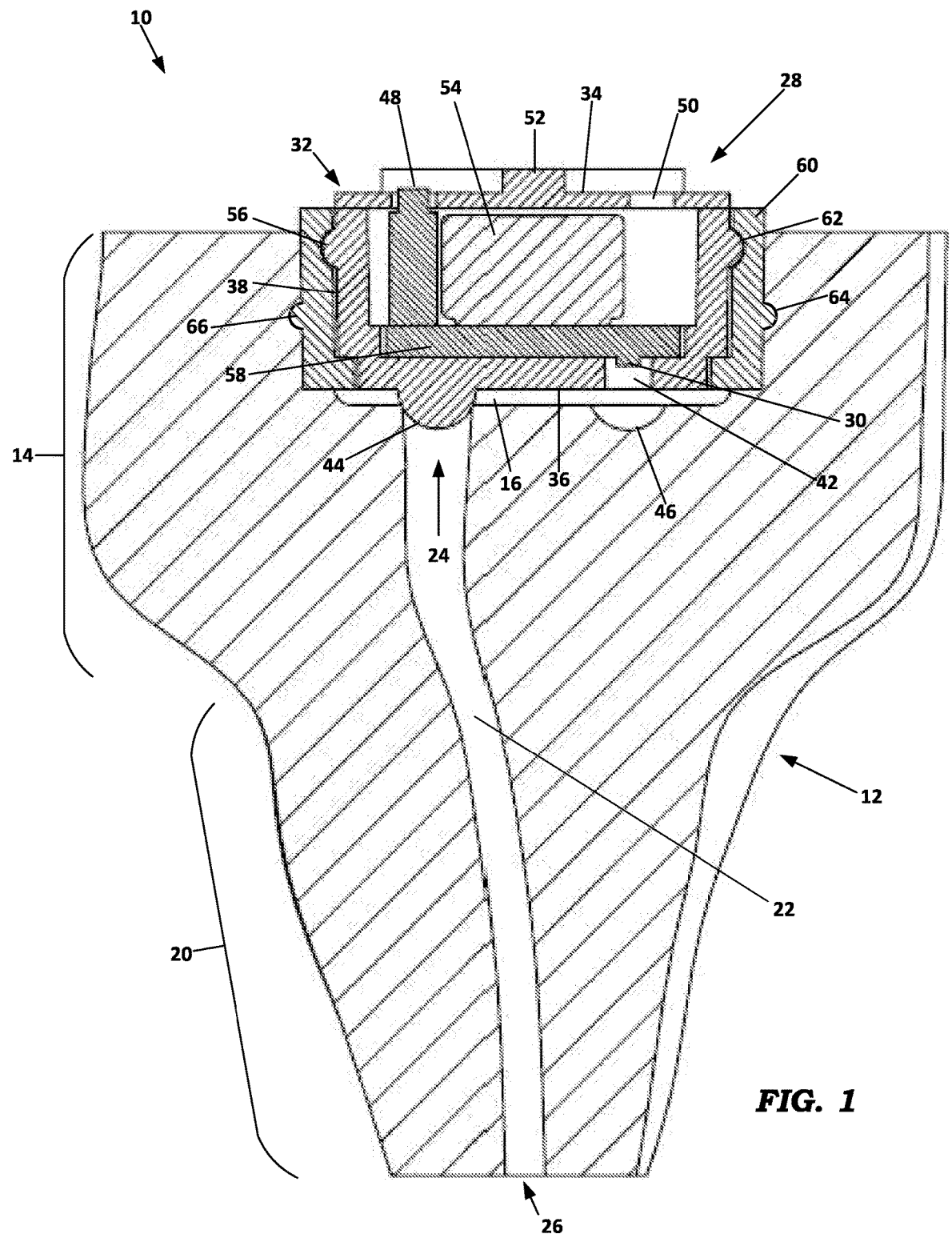
FIG. 1 depicts a cross-sectional side view of a hearing protection system in a hearing aid mode according to an embodiment of the invention.
Figure 2:
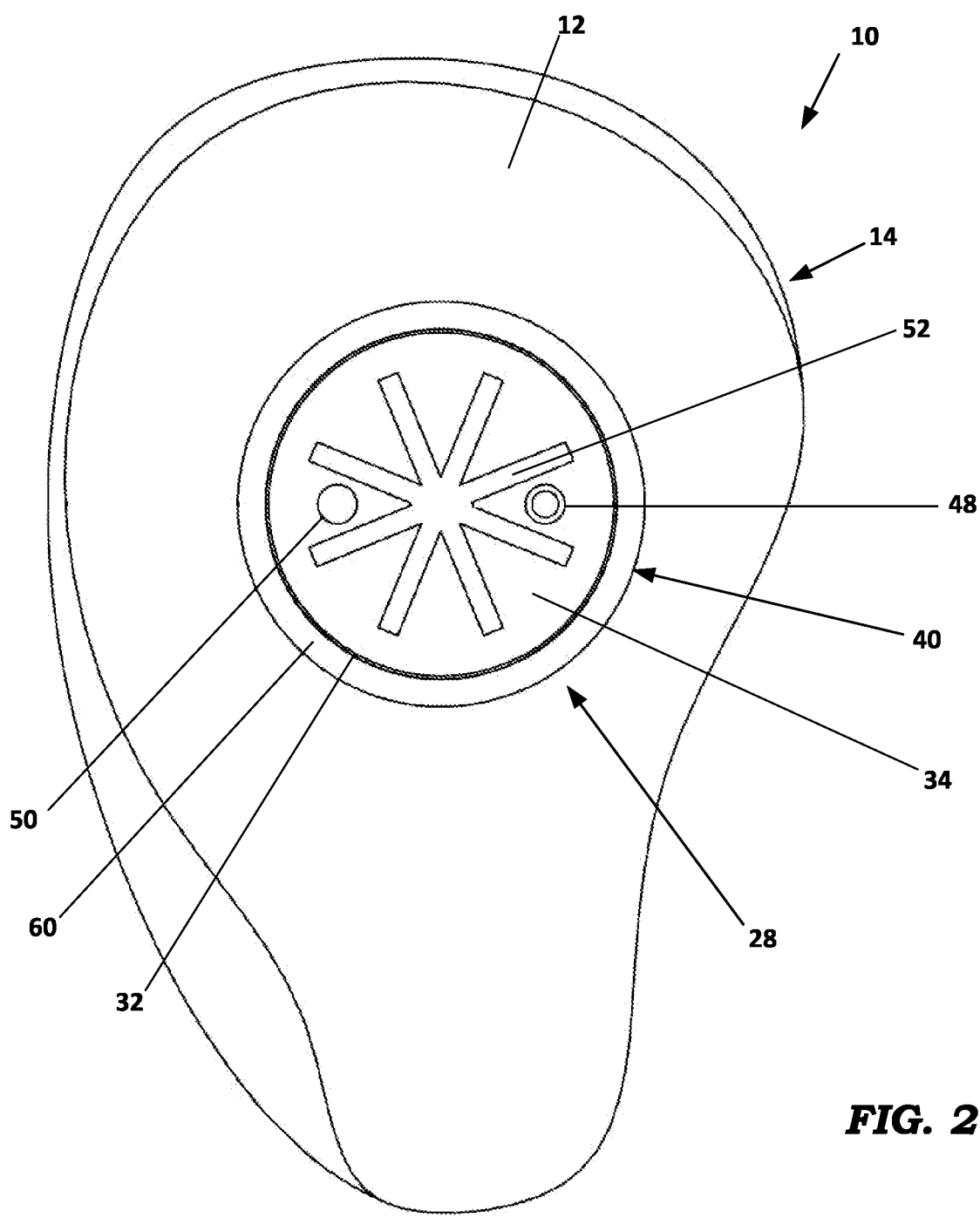
FIG. 2 depicts a top view of the hearing protection system.
Figure 3:
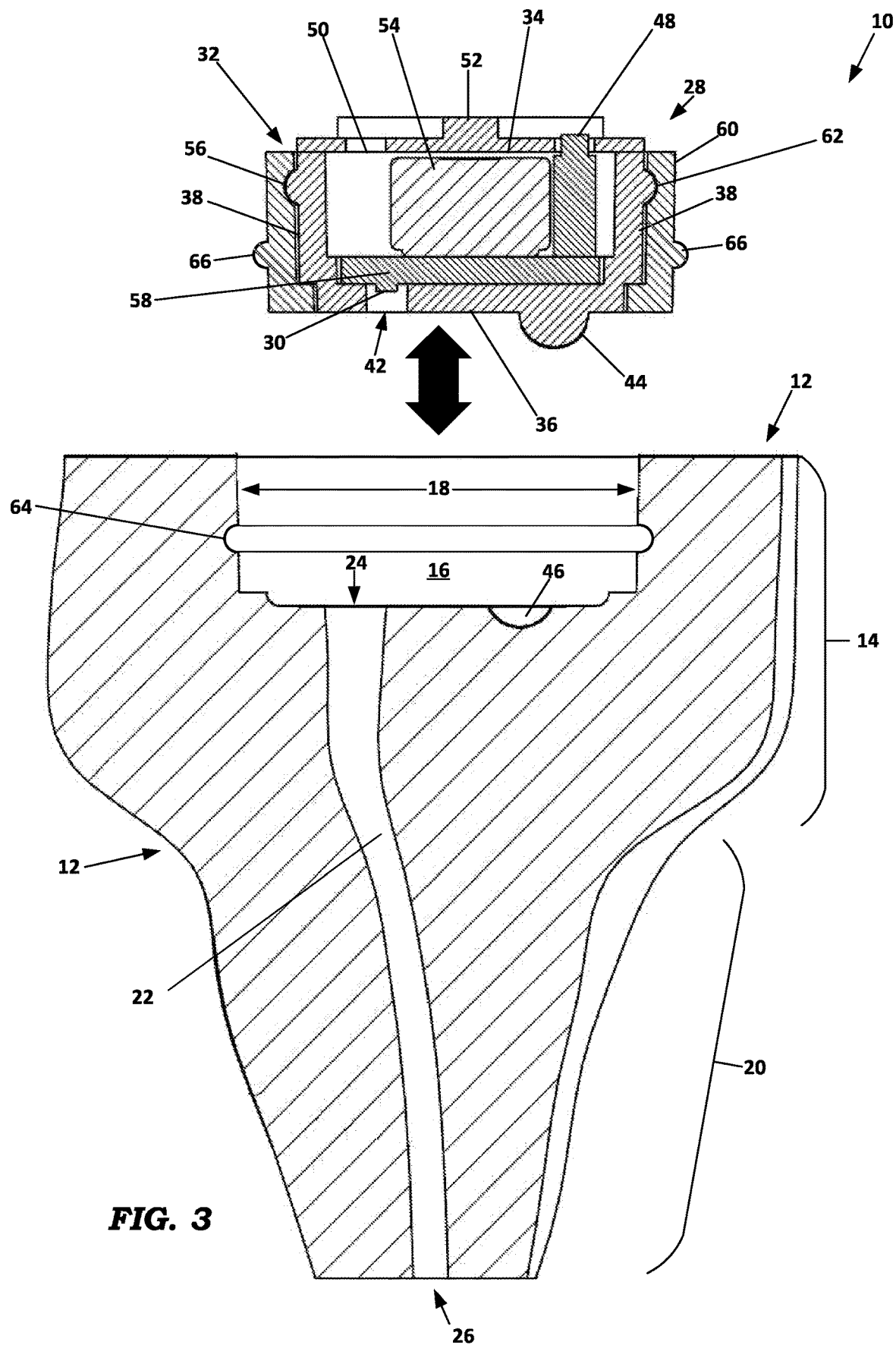

FIGS. 1-4 depict a custom electronic switchable hearing protection system 10. In some preferred embodiments, hearing protection system 10 includes an earplug 12 having a first portion 14 and a second portion 20. The first portion 14, which is configured to fit in the user's outer ear, contains a recessed cavity 16 having an inner profile 18, as depicted in FIG. 3. The second portion 20 is configured to precisely fit into a user's ear canal. In a preferred embodiment, the earplug is molded from silicone using a mold having dimensions based on laser measurements or digital imaging of the user's ear canal. Alternatively, an impression of the ear canal may be made by casting.

In a preferred embodiment, the earplug 12 includes a sound tube 22 extending through the first portion 14 and the second portion 20 of the earplug 12. The sound tube includes a first opening 24 disposed within the recessed cavity 16 of the first portion 14 and a second opening 26 disposed at a distal end of the second portion 20. In some configurations of the system 10, the sound tube 22 allows sound to travel through the first opening 24 to the second opening 26 and then into the user's ear canal.

In a preferred embodiment, the hearing protection system 10 includes an electronic hearing device 28 that is at least partially received within the recessed cavity 16 of the earplug 12. The electronic hearing device 28 includes a microphone 50 for receiving external sound, programmable electronics 58 for processing and amplifying the received sound according to the user's preferences, a pushbutton 48 for controlling the electronics, a battery 54 for powering the electronics, and a speaker 30 for generating the processed and amplified sound. The battery may be replaceable or rechargeable.

The electronic hearing device 28 includes a housing 32 having a front surface 34 and an opposing rear surface 36. In the preferred embodiment, the housing 32 includes a generally cylindrical side surface 38 aligned perpendicular to the front and rear surfaces 34-36. A speaker opening 42 is disposed in the rear surface 36 of the housing through which the sound generated by the speaker 30 is emitted. In the preferred embodiment, the housing 32 of the electronic hearing device 28 is molded from a sturdy plastic, such as Photoplastic, or formed from metal. In some embodiments, the housing 32 is an acrylic material in which the electronic components are encased (potted) for protection from moisture.

The preferred embodiment of the system 10 includes a generally cylindrical outer ring 60 that surrounds the side surface 38 of the housing 32. As described in more detail hereinafter, the housing 32 is operable to rotate within the outer ring 60.

In a preferred embodiment, the electronics 58 incorporate programmable digital signal processing that provides for personalizing the electronic hearing device 28 to accommodate the hearing needs of the user based on user-selected algorithms. Examples of hearing assistance devices that incorporate such programmable digital signal processing are described in U.S. Pat. Nos. 7,974,716B2, 8,265,314B2, 8,284,968B2, 8,396,237B2, 8,077,890B2, 8,472,634B2, 8,811,642B2 and 9,031,272B2, the entire disclosures of which are incorporated herein by reference. In some embodiments, only one preset program is provided for amplification, in which case no user selection of programs is needed.

In a preferred embodiment, the push button 48 is configured to allow the user to cycle the electronic hearing device 28 between different settings, including at least two different user-selected signal processing algorithms. In some embodiments, the push button 48 is also configured to be pressed by a user to power-on or power-off the electronic hearing device 28. In some embodiments, the push button 48 also can be used to adjust the volume of the sound generated by the speaker 30.

In a preferred embodiment, the hearing protection system 10 includes a grip portion 52 extending outward from the front surface 34 of the housing 32. The grip portion 52 is configured to be gripped by the user for rotating the housing 32 within the recessed cavity 16. In some embodiments, the grip portion 52 is comprised of a rotatable circular structure with at least one tab to be gripped by the user. In an alternative embodiment, the grip portion 52 comprises a knurled knob that extends outward from the front surface 34.

As shown in FIG. 2, the outer ring 60 has an outer profile 40 that is configured to correspond to the inner profile 18 of the recessed cavity 16 of the earplug 12. The outer profile 40 and inner profile 18 are configured so that the electronic hearing device 28 is held securely within the earplug 12, but also to allow the electronic hearing device 28 to be easily be removed and replaced by the user, such as when the charge on the battery 54 is depleted. In a preferred embodiment, the friction force between the outer profile 40 and the inner profile 18 is larger than the friction force between the outer ring 60 and the housing 32, so as to allow the user to rotate the housing 32 within the outer ring 60 without causing rotation of the outer ring 60 within the recessed cavity 16.

In a preferred embodiment, at least one annular retainer protrusion 66 extends outward from the cylindrical side surface 38 of the outer ring 60. The retainer protrusion 66 is received with a corresponding annular retainer channel 64 in the inner surface of the recessed cavity 16. This arrangement ensures that the electronic hearing device 28 is retained within the recessed cavity 16 until a user intentionally removes the electronic hearing device 28 from the cavity 16 by applying a sufficient pulling force.

Also in a preferred embodiment, at least one annular protrusion 56 extends outward from the cylindrical side surface 38 of the housing 32. The protrusion 56 is received with a corresponding annular channel 62 in inner surface of the outer ring 60. This arrangement keeps the housing 32 locked into the outer ring 60, while allowing the housing 32 to rotate within outer ring 60 when a rotational force is applied to the housing 32.

In a preferred embodiment, the housing 32 is configured to be rotatable within the outer ring 60 between multiple positions, including a first position and a second position. In the first position, the speaker opening 42 aligns with the first opening 24 of the sound tube 22, thereby permitting the sound generated by the speaker 30 to propagate through the sound tube 22 to the second opening 26. In the second position, the rear surface 36 of the housing 32 at least partially blocks the first opening 24 of the sound tube 22, thereby at least partially preventing sound from entering the sound tube 22. In the preferred embodiment, the housing 32 is configured to rotate 180 degrees from the first position to the second position. However, it will be appreciated that the first and second positions could be rotationally spaced apart at other angles.

In some embodiments, the electronic hearing device 28 includes a protrusion 44 extending outward from the rear surface 36 of the housing 32 and spaced apart from the speaker opening 42 of the housing 32. The protrusion 44 is configured to align with and at least partially block the first opening 24 of the sound tube 22 when the housing 32 is rotated to the second position. In some embodiments, an indentation 46 is disposed within the surface of the recessed cavity 16 that engages the rear surface 36 of the housing 32. The indentation 46 is configured to at least partially receive the protrusion 44 when the housing 32 is in the first position.

In some embodiments, when a loud noise is detected by the microphone 50, the programmable electronics 58 of the electronic hearing device 28 utilizes a fast compression algorithm to quickly attenuate the corresponding sound provided to the speaker 30 so that the sound that reaches the user's ear canal will not cause hearing damage. The fast compression algorithm preferably has a fast-acting attack time of between 0.5 msec and 20 msec to implement the attenuation. In a preferred embodiment, the programmable electronics 58 remove the attenuation when the excessive loud noise ceases, thereby returning to normal operation. The attack time is preferably a programmable preset value.

Figure 4:
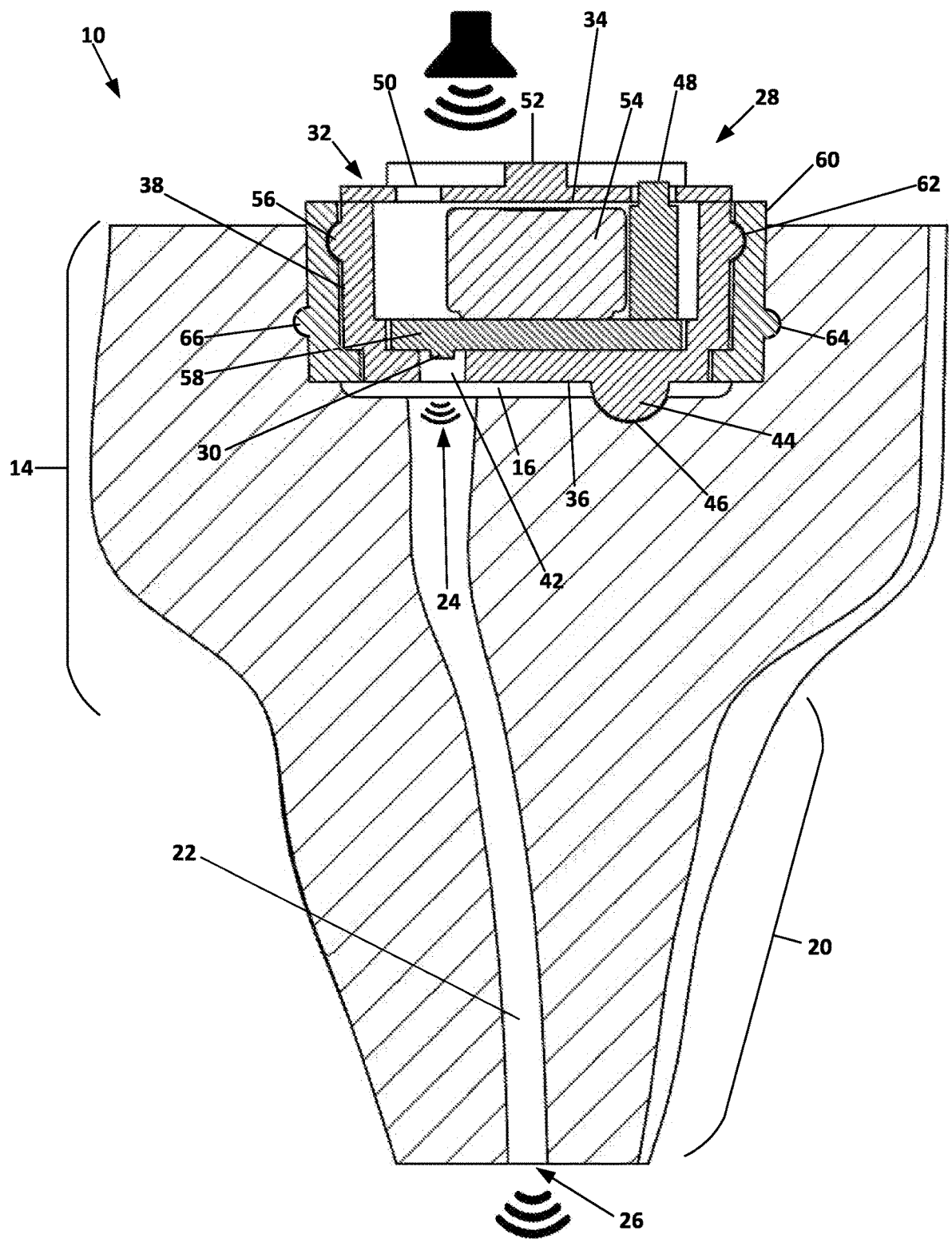
FIG. 4 depicts a cross-sectional side view of the hearing protection system in a hearing protection mode according to an embodiment of the invention.

FIG. 4 depicts a preferred embodiment of the hearing protection system 10 in the active hearing aid mode. The external sound is received through the microphone 50 and is provided to the programmable electronics 58 of the electronic hearing device 28. The programmable electronics 58 process and amplify the sound signal, which is provided to the speaker 30 to generate audible sound at the speaker opening 42. The sound from the speaker 30 propagates into the first opening 24 of the sound tube 22 and through the sound tube 22 to the second opening 26 and into the user's ear canal.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A hearing protection system comprising:
    an earplug comprising:
        a first portion configured to be disposed in a user's outer ear, the first portion including a recessed cavity having an inner profile;
        a second portion having a distal end configured for insertion into the user's ear canal;
        a sound tube extending through the first and second portions of the earplug, the sound tube having:
            a first opening disposed within the recessed cavity of the first portion; and
            a second opening disposed at the distal end of the second portion; and
    an electronic hearing device received at least partially within the recessed cavity of the earplug, the electronic hearing device comprising:
        a speaker for generating sound;
        a housing in which the speaker and other electronic components of the electronic hearing device are disposed, the housing having:
            a front surface;
            a rear surface opposite the front surface;
            a side surface disposed between the front and rear surfaces; and
            a speaker opening disposed in the rear surface, the speaker opening for emitting the sound from the speaker;
        wherein the housing is rotatable between multiple positions, including:
            a first position in which the speaker opening aligns with the first opening of the sound tube, thereby permitting the sound generated by the speaker to propagate through the sound tube to the second opening; and
            a second position in which the rear surface of the housing at least partially blocks the first opening of the sound tube, thereby at least partially preventing sound from entering the sound tube.

2. The hearing protection system according to claim 1, further comprising a grip portion extending outward from the front surface, the grip portion configured to be gripped by the user for rotating the housing with respect to the recessed cavity.

3. The hearing protection system according to claim 2, wherein the grip portion comprises a rotatable circular structure with at least one outwardly extending tab configured to be gripped by the user.

4. The hearing protection system according to claim 1, wherein the earplug is shaped to fit the shape of the user's ear canal.

5. The hearing protection system according to claim 1, wherein the earplug is made of silicone.

6. The hearing protection system according to claim 1, wherein the housing of the electronic hearing device is made of plastic.

7. The hearing protection system according to claim 1, wherein the electronic hearing device incorporates digital signal processing that is programmable according to the user's hearing profile.

8. The hearing protection system according to claim 1, wherein the housing is rotated by 180 degrees from the first position to the second position.

9. The hearing protection system according to claim 1 further comprising a protrusion extending outward from the rear surface and spaced apart from the speaker opening of the housing, wherein the protrusion aligns with and at least partially blocks the first opening of the sound tube when the housing is rotated to the second position.

10. The hearing protection system according to claim 1, further comprising an indentation in a surface of the recessed cavity that engages the rear surface of the housing, the indentation configured to at least partially receive the protrusion when the housing is in the first position.

11. The hearing protection system according to claim 1, further comprising a push button disposed on the front surface of the housing of the electronic hearing device, the push button configured to be pressed by a user to power-on or power-off the electronic hearing device, and to adjust the sound generated by the speaker.

12. The hearing protection system according to claim 1, wherein the electronic hearing device includes a battery for supplying power to the components of the electronic hearing device.

13. The hearing protection system according to claim 1, wherein the inner profile of the recessed cavity is cylindrical and the side surface of the housing is cylindrical.

14. The hearing protection system according to claim 1, wherein the electronic hearing device incorporates fast compression programming to shut off sound amplification to protect the user when a loud noise is detected, and to resume amplification after the loud noise ends.

15. The hearing protection system according to claim 1, wherein the housing includes an annular protrusion extending outward from the side surface of the housing, and wherein the hearing protection system includes an outer ring disposed around the side surface of the housing to surround the electronic hearing device, and wherein the outer ring has an outer profile configured to correspond to the inner profile of the recessed cavity, and wherein the outer ring includes an annular channel on an inner surface of the outer ring, the annular channel configured to engage the annular protrusion on the housing to secure the housing within the outer ring while allowing the housing to rotate when a rotational force is applied to the housing.

* * * * *